United States Patent

Buck et al.

Patent Number: 5,996,422
Date of Patent: Dec. 7, 1999

[54] BUCK AIR SAMPLING PUMP FLOW CONTROL ALGORITHM

[75] Inventors: Albert P. Buck; Michael S. Buck, both of Orlando; Timothy R. Geis, Altamonte Springs, all of Fla.

[73] Assignee: A.P. Buck, INc., Orlando, Fla.

[21] Appl. No.: 08/865,729

[22] Filed: May 30, 1997

[51] Int. Cl.[6] .................................................. G01N 1/24
[52] U.S. Cl. .................................. 73/863.03; 73/863.23; 702/25
[58] Field of Search ........................... 73/863.02, 863.03, 73/863.23, 864.34, 864.35, 863.24, 863.25; 702/25

[56] References Cited

U.S. PATENT DOCUMENTS

| | | | |
|---|---|---|---|
| 4,269,059 | 5/1981 | Baker ..................................... | 73/863.03 |
| 4,375,667 | 3/1983 | Buchan ............................ | 73/863.23 X |
| 4,389,903 | 6/1983 | Berune et al. ......................... | 73/863.03 |
| 4,893,515 | 1/1990 | Uchida ................................. | 73/864.34 |
| 5,090,257 | 2/1992 | Bruce ..................................... | 73/863.03 |
| 5,107,713 | 4/1992 | Peck et al. ............................ | 73/863.02 |
| 5,163,818 | 11/1992 | Betsill et al. ..................... | 73/863.03 X |
| 5,576,503 | 11/1996 | Nabity et al. ..................... | 73/864.34 X |
| 5,646,357 | 7/1997 | Ogden et al. ..................... | 73/863.23 X |
| 5,717,147 | 2/1998 | Basch et al. ......................... | 73/863.23 |

*Primary Examiner*—Thomas P. Noland
*Attorney, Agent, or Firm*—James H. Beusse; Holland & Knight LLP

[57] ABSTRACT

A method for controlling an air sampling pump includes establishing from empirical measurement a family of sets of data relating speed of the pump to the flow rate of air through the pump as a function of pressure drop of the air at the pump inlet and storing the data in an electronic memory. The pump is then operated at a selected speed corresponding to a desired air flow rate and selected inlet pressure drop. The actual pressure drop is measured and a pair of sets of pressure drop values are identified in the stored data, which values bracket the actual measured pressure drop. The desired air flow rate and corresponding pump RPM value for each of the identified pair of sets of differential pressure values are located and extrapolation is used to locate a new value of RPM for delivering the desired air flow rate at the actual measured value of pressure drop. The pump is then operated at the new RPM value.

7 Claims, 5 Drawing Sheets

GENIE EXTRA

H₂O

| T1 | A | B | C | D | E | F | G | H | I | J |
|----|---|---|---|---|---|---|---|---|---|---|
|    | FLOW | 0 | 1 | 2 | 5 | 10 | 20 | 30 | 40 | 50 |
| 1  | 0 |   |   |   |   |   |   |   |   |   |
| 2  | 500 |   |   |   |   |   |   |   |   |   |
| 3  | 1000 |   |   |   |   |   |   |   |   |   |
| 4  | 1220 |   |   |   |   |   |   |   |   |   |
| 5  | 1342 |   |   |   |   |   |   |   |   |   |
| 6  | 1583 |   | RPM |   |   |   |   |   |   |   |
| 7  | 1680 | 600 | 800 | 870 | 1050 | 1020 | 1010 | 1140 | 1300 |   |
| 8  | 2000 | 720 | 1000 | 1030 | 1144 | 1180 | 1230 | 1330 | 1480 |   |
| 9  | 3000 | 1200 | 1500 | 1550 | 1628 | 1730 | 1860 | 2030 | 2100 |   |
| 10 | 4000 | 1650 | 2000 | 2080 | 2130 | 2250 | 2390 | 2610 | 2900 |   |
| 11 | 5000 | 2100 | 2500 | 2550 | 2650 | 2748 | 3100 | 3370 | 3572 |   |
| 12 | 5700 | 2400 | 2700 | 2800 | 2900 | 3100 | 3450 | 3650 | 4000 |   |
| 13 | 6000 | 2600 | 2850 | 3000 | 3090 | 3315 | 3640 | 3800 |   |   |
| 14 | 6544 | 2800 | 3200 | 3220 | 3300 | 3500 | 3800 | 4100 |   |   |
| 15 | 7000 | 3000 | 3400 | 3430 | 3600 | 3735 | 4019 | 4300 |   |   |
| 16 | 7400 | 3200 | 3600 | 3650 | 3800 | 3950 | 4250 | 4500 |   |   |
| 17 | 8000 | 3400 | 3800 | 3850 | 4050 | 4250 | 4500 |   |   |   |
| 18 | 8364 | 3600 | 3950 | 4200 | 4350 | 4450 | 4750 |   |   |   |
| 19 | 9000 | 3900 | 4200 | 4400 | 4510 | 4700 | 5100 |   |   |   |
| 20 | 9690 | 4200 | 4350 | 4800 | 4900 | 4950 |   |   |   |   |
| 21 | 10000 | 4400 | 4600 | 5000 | 5100 | 5460 |   |   |   |   |
| 22 | 10500 | 4600 | 4900 | 5350 |   |   |   |   |   |   |
| 23 | 11000 | 4800 | 5300 |   |   |   |   |   |   |   |

FIG. 5

BUCK AIR SAMPLING PUMP FLOW CONTROL ALGORITHM

BACKGROUND OF THE INVENTION

This invention relates to battery powered air sampling pump systems and, more particularly, to a pump system for maintaining constant air flow rate.

U.S. Pat. No. 5,107,713 (the "'713 patent"), assigned to the assignee of the present invention, describes a portable air sampling pump system of the type generally carried or worn by a person in order to collect environmental air samples for determining air quality. The pump system of the '713 patent comprises an air sampling pump having a central processing unit (CPU) for developing pulse width modulation (PWM) control signals for application to a PWM motor driver which is connected to supply electric power to a DC electric motor. The motor is coupled in driving relationship to a diaphragm type air pump and a revolution per minute (RPM) counter is coupled to the motor/pump assembly for providing RPM signals representative of pump speed to the CPU. The CPU includes memory operably associated with it for storing data indicative of predetermined relationships between RPM, PWM and air flow. The CPU is responsive to a commanded air flow signal for generating a corresponding PWM signal for energizing the motor at a preselected RPM. The relationship between motor RPM and air flow rate is obtained by a combination of empirical measurement and interpolation. In one form, the pump is initially energized at a preselected PWM value and the pump flow rate and RPM corresponding to that PWM value are recorded. The pump is then energized at another PWM value and the pump flow rate and RPM corresponding to that value are also recorded. These two values enable development of a characteristic curve for the pump. Tables of PWM values relating RPM and flow rate to PWM are computed from the two measured values. When a desired flow rate is set in the CPU, the CPU generates a PWM signal to energize the pump at an RPM corresponding to the desired flow rate. Thereafter, the RPM of the pump is monitored and the PWM value periodically adjusted to maintain the RPM at the selected value.

While the system described in the '713 provides relatively accurate control of air flow rate, it is not as precisely accurate as is desirable when measurement of some air borne contaminants are being monitored at concentrations measured in parts per million. The '713 patent system uses the assumption that air flow rate is directly approximate to pump RPM. However, a more accurate measurement is needed to accommodate variations in the system such as may be caused by clogging of an input filter designed to remove dust or other debris from the air being sampled.

SUMMARY OF THE INVENTION

The present invention improves on the air sampling pump system of U.S. Pat. No. 5,107,713 by incorporating apparatus for indirectly measuring air flow and using such measurement to adjust the motor/pump RPM in order to maintain air flow at a selected value. In an air sampling pump system such as that described in the '713 patent, a filter is placed in an air inlet line to the pump for removing airborne particulate matter from the air prior to the air entering the pump. The present invention incorporates an air pressure sensor between the filter and air pump in order to measure the pressure drop across the filter. Preferably the pressure sensor is a differential sensor having one side open to atmosphere and the other side connected to monitor the pressure at the pump inlet. As a consequence, the pressure sensor actually measures the pressure drop across the input filter. It is well known that the pressure drop across a flow impedance is directly proportional to the volume of flow through the impedance. Consequently, measurement of the differential pressure across the filter is directly proportional to the volume of air flow through the filter.

In the present invention, applicant uses a differential pressure sensor to monitor the inlet pressure to the pump and thereby provide a direct measurement of the pressure drop across the input filter. In a calibration mode, applicant measures the actual flow through a filter pump combination for a plurality of values of pump inlet pressure as a function of RPM of the pump. This measurement provides a set of curves of RPM versus flow at various differential pressures. All of these values are then stored in memory in the microprocessor based control for the pump motor, the control being substantially as described in the '713 patent. When the air sampling pump system is in use, the user or environmental hygienist will set a desired flow rate in the pump controller and the controller will automatically adjust the pump motor RPM to obtain this flow rate based upon measured values of differential pressure. In particular, the algorithm operating in the microprocessor based controller senses the requested flow rate, obtains a reading of the differential pressure across the inlet filter and then identifies the RPM versus flow rate curves which are nearest to the value of the measured differential pressure. Assuming that the measured differential pressure actually falls between two adjacent curves, the system interpolates from the actual curves a value of RPM which is necessary to achieve the desired flow rate at the measured pressure. Accordingly, the pump is operated at an RPM which will assure that the desired flow rate is met by the pump/motor combination.

BRIEF DESCRIPTION OF THE DRAWINGS

For a better understanding of the present invention, reference may be had to the following detailed description taken in conjunction with the accompanying drawings in which:

FIG. 5 is a chart of data for generating the curves of FIG. 3.

DETAILED DESCRIPTION OF THE INVENTION

Figure 1:
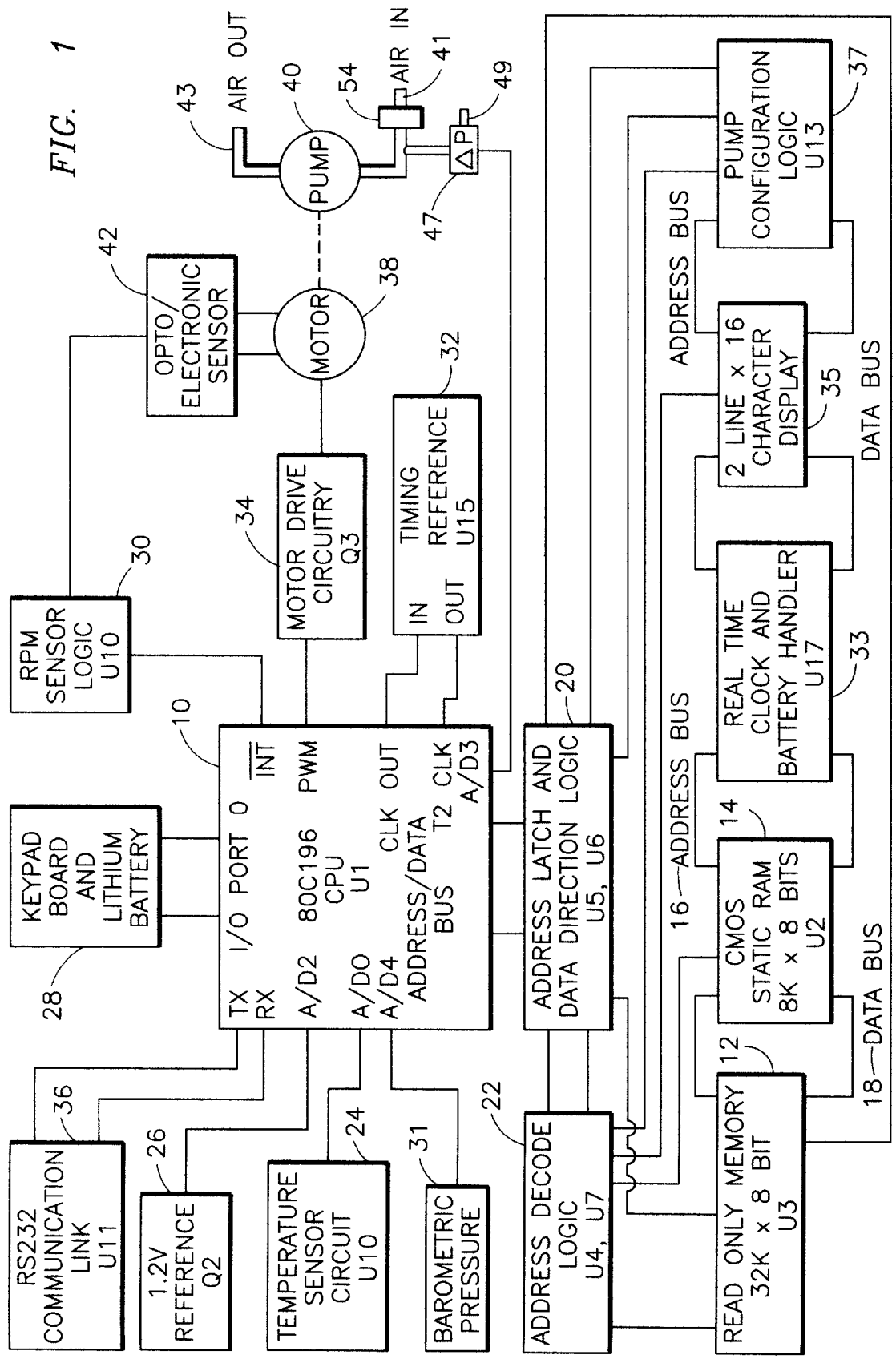
FIG. 1 is a simplified block diagram of one embodiment of an air pump system with which the present invention may be used.

FIG. 1 illustrates a block diagram of one implementation of the present invention. This implementation is based upon a microprocessor and, in particular, a type 80C196 central processor unit (CPU) indicated at 10 having read only memory (ROM) address bus 16 and data bus 18 through an address latch and data direction logic circuit 20. An address decode logic circuit 22 is also connected onto the address bus and to various peripherals on the buses. The CPU 10 is connected via various I/O ports for receiving data input from a temperature sensor circuit 24, a voltage reference 26, a keyboard 28, an RPM sensor logic 30, a barometric pressure sensor 31, and a timing reference 32. A real time clock 33 and a pump configuration logic circuit 37 are also connected to the CPU 10. A 2 line ×16 character LCD display 35 is coupled to the data and address buses 16, 18. The CPU 10 includes internal logic circuits for generating PWM signals at an I/O port for delivery to a motor drive circuit 34 and a transmit (TX) and receive (RX) port for connection to a communication link 36. A rechargeable lithium battery is physically mounted to the keyboard and provides power to maintain CPU RAM in the event of loss of primary power. Primary power is provided by a rechargeable nickel-cadmium battery pack (not shown).

The motor driver circuit 34 is coupled in driving relationship to a direct current (DC) electric motor 38. A shaft of motor 38 is coupled to drive a bellows-type air pump 40, and an opto-electronic sensor 42 is positioned for providing an actual count of the cycles per minute of the pump. Since the pump completes one cycle for each revolution of the motor shaft, pump speed can be expressed in shaft revolutions per minute (RPM) and such term is used herein to define pump speed. Sensor 24 provides the RPM count to RPM sensor logic 30 which conditions the count to a form acceptable by CPU 10. The pump 40 draws air in through air inlet 50 and filter 54 with the air exiting through exhaust 58. A differential pressure sensor 47 measures pressure at the pump side of filter 54. Sensor 47 is preferably a piezoelectric sensor such as the Motorola MPX12 having an opening 49 to atmosphere. An LCD display 35 provides direct readout of selected data including input data such as commanded or desired flow rates, PWM and RPM values, differential pressure and various status messages and error signals.

Figure 2:
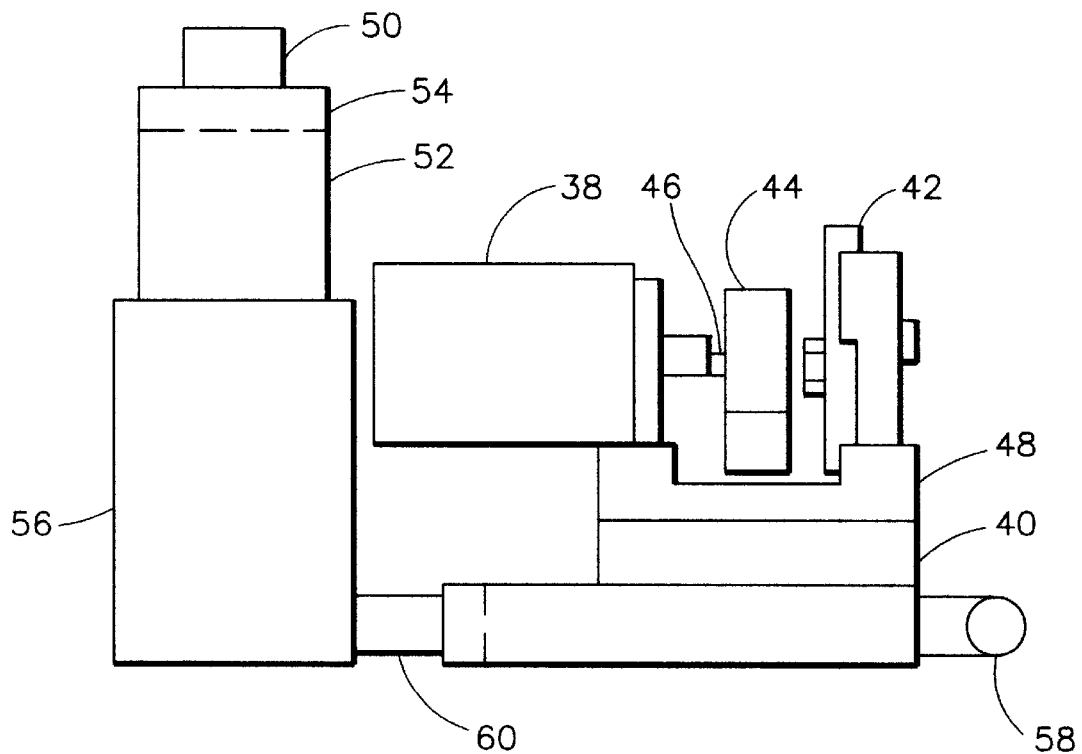
FIG. 2 is an elevation view of an air sampling pump arrangement.

FIG. 2 is a simplified elevation view of the pump 40 illustrating the arrangement of motor 38 and sensor 42. The pump 40 may be a commercially available pump such as that available from CASSELLA Ltd. of England which uses a flexible diaphragm that can be driven by a cam actuated lever 44 coupled to motor shaft 46. The opto-electronic sensor 42 is mounted to pump body 48 adjacent lever 44 and opposite motor 38, also mounted to pump body 48. The sensor 42 could monitor rotation of the rotor shaft 46 using a conventional reflective surface but preferably is positioned to monitor movement of the pump by sensing light interruption as the moveable diaphragm of the pump is displaced in front of the sensor. Since the pump completes one cycle for each revolution of motor shaft 46, the time between each light interruption represents the time for one revolution of shaft 46. An air inlet 50 is formed as part of a support 52 for an inlet filter or particulate collector 54. Air passing through filter 54 enters a damper 56 which tends to smooth pulsations created by operation of the diaphragm type pump. The damper 56 may be a chamber formed with at least one wall of a thin flexible material such as Neoprene rubber. Exhaust air exits through exhaust port 58.

The system of U.S. Pat. No. 5,107,713 established a relationship between air flow rate and pump RPM based upon an assumption that RPM and flow rate were directly correlated. While such relationship is a good approximation, various factors affect this relationship. A better measurement of flow rate is therefore desirable. Applicants have found that one such measurement is pressure drop across the air inlet filter 54. It is known that pressure drop across a fixed size orifice is directly related to the volume rate of fluid flow through the orifice for subsonic flow rates. The inlet filter 54 does not represent an ideal orifice but does have definable pressure vs. flow rate characteristics. A typical filter 54 is an in-line 37 mm cassette filter of mixed cellulose esters forming a membrane with 0.8 micron capture capacity.

Filter differential pressure is also effected by the characteristics of the pump 40. The pump 40 is a diaphragm type pump in which the volume of air moved per stroke varies with the stroke rate, i.e., the volume flow is not directly proportional to motor RPM. Accordingly, in order to define flow rate as a function of differential pressure across the inlet filter 54, it is necessary to create a family of curves or graphs representing flow rate as a function of motor RPM for each of a plurality of differential pressure values.

Figure 3:
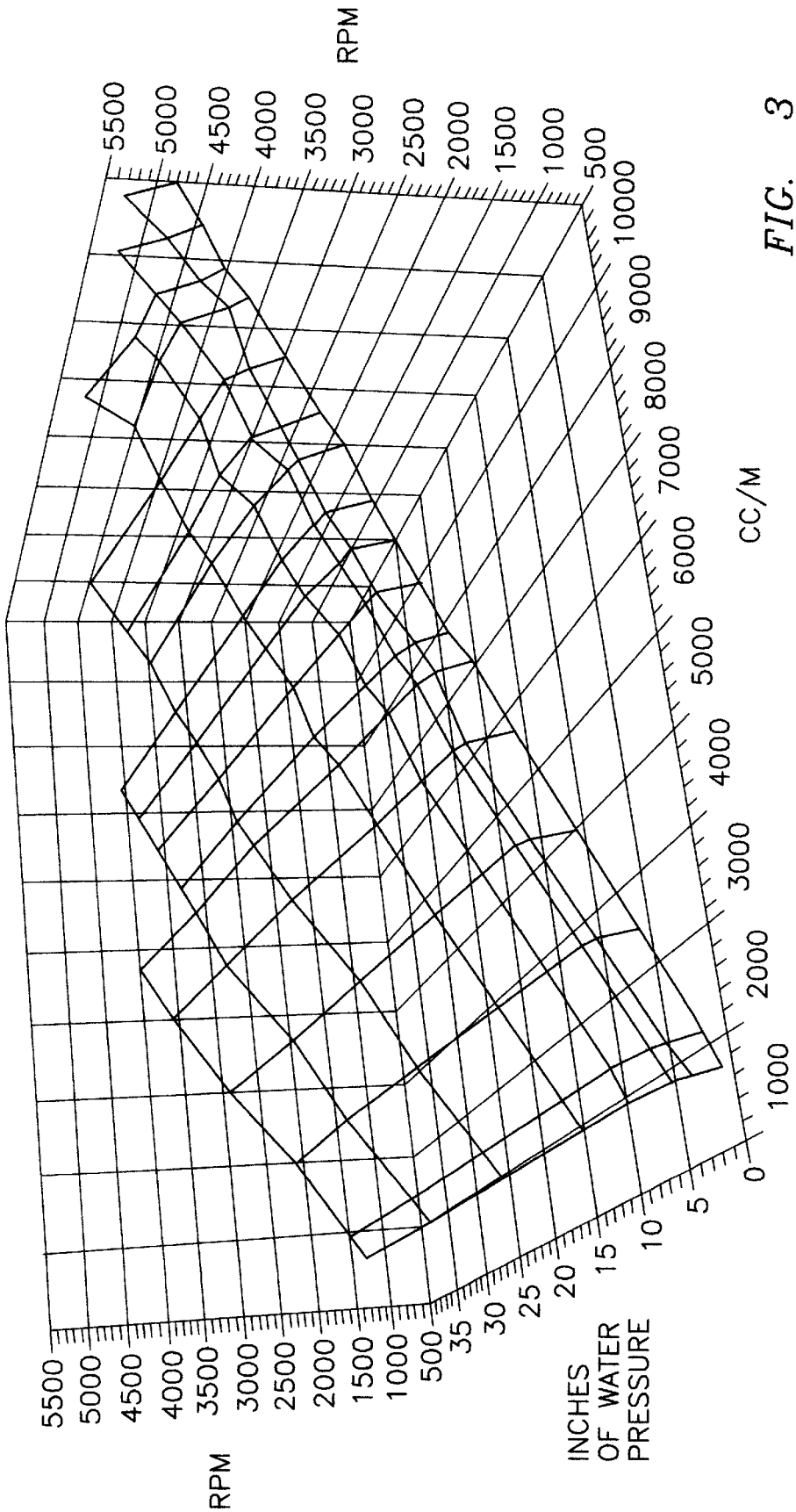
FIG. 3 is a set of characteristic curves for an air sampling pump.

One method of establishing the family of graphs is to operate the pump at varying speeds while measuring actual flow rate. In order to obtain flow rate values at different differential pressures, the filter 54 can be replaced by an in-line controllable orifice such as a needle valve. The motor 38 is energized at some selected minimum speed and the valve adjusted to establish a desired differential pressure. Air flow rate is then measured using an air flow standard such as the MiniBuck flowmeter available from A. P. Buck, Inc. of Orlando, Fla. The combination of motor speed or RPM, differential pressure and measured air flow establishes a first point on a graph of constant differential pressure. Additional points on the graph are thereafter located by repeatedly increasing motor speed to selected values, setting the desired value of differential pressure by adjusting the needle valve and measuring air flow at each new motor speed. The family of graphs is established in a similar manner by selecting different values of differential pressure and repeating the steps of setting motor speed and measuring air flow. The final result is a family of characteristic curves such as shown in FIG. 3 which define a three-dimensional plane relating motor speed (RPM) differential pressure (AP) and air flow rate (FLOW). With these graphs, any two of the variables will define the third.

As described with reference to FIG. 2, the motor 38 drives a cam 44 mounted on the motor shaft, which cam engages diaphragm pump 40 causing the pump to execute one pump cycle for each revolution of the motor shaft. In order to assure that the system rapidly settles at the motor speed which will produce the desired flow rate, it is necessary to provide a method for quickly determining motor speed or RPM. In a preferred embodiment, the sensor 42 provides a pulse signal each time the pump cycles. The pulse signal is supplied to the CPU 10 which measures the time between successive pulses and converts that time into speed or RPM allowing motor speed to be determined within the time for one pump cycle. For a motor speed of between 500 and 6000 RPM, motor speed is determined from about 8 to 100 times per second thus providing the rapid response necessary to allow the desired air flow to be established within a few cycles of pump operation.

Figure 4:
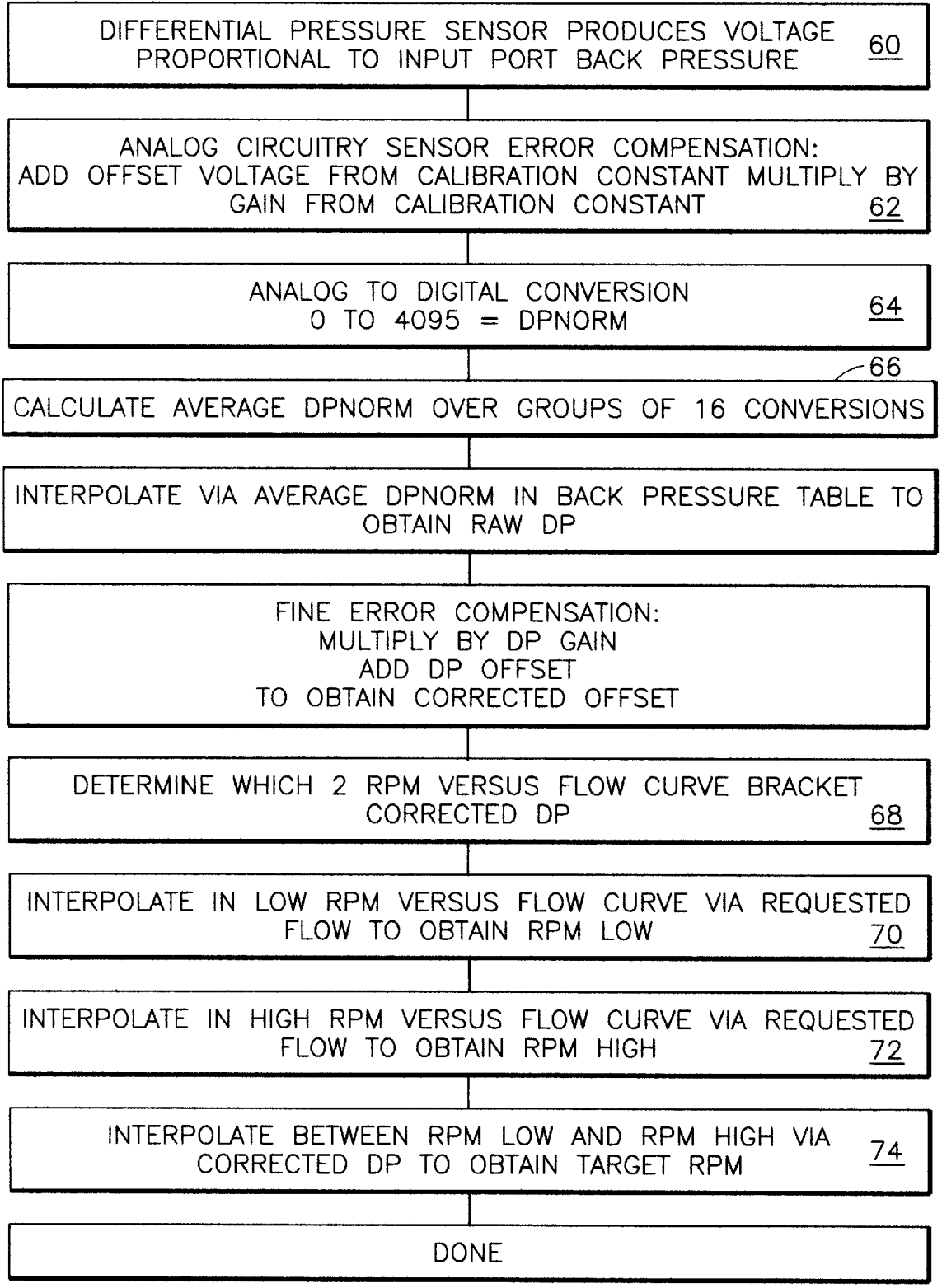
FIG. 4 is a flow chart of a method implementing at least part of the present invention.

The method by which the CPU 10 determines a motor speed necessary to establish a desired air flow rate using the graphs of FIG. 3 is shown in the flow chart of FIG. 4. For purpose of simplifying understanding of the method, specific values will be assumed such as a desired air flow rate of 2000 ML per minute and a family of curves for differential pressure values between about 1 and 40 inches of water. The desired flow rate is normally set prior to starting the pump 40 and in this example would b set at 2000 ML. When power is applied and after a short time delay to allow the system to stabilize, the initial reading of differential pressure (DP) is obtained from sensor 47, block 60. In one embodiment, the sensor 47 is a piezoelectric differential pressure sensor available from Motorola Corporation under their Model MPX10/MPX12 series designation, and has one inlet open to atmosphere and another inlet coupled to the pump inlet so as to measure the differential pressure across the inlet filter 54. While these devices provide output signals proportional to differential pressure, applicants have found that device characteristics are widely divergent. Accordingly, each device must be calibrated and compensation provided to normalize readings from different devices. Block 62 represents analog compensation of the signal received from a particular sensor 47. After compensation, the analog sensor signal is converted to a digital signal using a conventional A/D converter, block 64, producing the signal DPNORM. Preferably, the method uses an average value of DPNORM obtained by average a selected number of DP readings, e.g., 16 readings, as indicated by block 66.

In block 68, the value of the average DPNORM signal is converted to a differential pressure value in inches of water. Once the value of DP is determined, the CPU 10 identifies the two differential pressure curves which bracket the actual measured value, block 68. Actually, the graph of FIG. 3 is a visual interpretation of the data stored in CPU memory (typically EPROM). The actual data appears as shown in the table of FIG. 5 and the step of block 68 requires selecting of values from the table. For example, if the measured value of DP is 15 inches of water and the desired value of air flow is 2000 ML (CC per minute), the CPU 10 identifies the bracketing values of 1180 RPM at 10 inches of water and 1230 RPM at 20 inches of water. These two steps of selecting the low and high RPM values are indicated at blocks 70 and 72. Once the low and high RPM values are obtained, the CPU interpolates to identify an RPM value corresponding to the measured DP and desired flow rate, block 74. In this example, the interpolated value is [(15−10)/(20−10)] (1230−1180)+1180 or 1205 RPM to deliver 2000 ML at a DP of 15 inches of water.

The pump control system of FIG. 1 also enables constant volume sampling with changes in atmospheric pressure and temperature. The table values of FIG. 4 are provided for a standard temperature (for example, 25° C.) and sea level pressure of 760 mm Hg. If constant volumetric flow (volume of air per unit time) is selected as an operating mode, the system will operate as described above to maintain constant volumetric flow. If constant mass flow is selected, the system will automatically control pump speed so as to collect or pass a selected mass of air per unit time. For example, a flow rate of 2000 cc/min at sea level would have to increase to 3000 cc/min at 10,000 ft. to maintain the same mass flow since the atmosphere is rarified at altitude.

The relationship between mass flow at sea level (standard temperature and pressure or STP) and mass flow at other conditions is given by:

$$Vol(STP) = Vol_1 \left[ \frac{P_1}{P} \cdot \frac{298}{T_1^\circ C + 273} \right]$$

where $Vol_1$ is the volumetric flow rate at pressure $P_1$ and temperature $T_1$, P is in mm Hg (760 mm at sea level) and 298 represents 25° C. in degrees Kelvin. Once the volumetric flow is set in STP values, the system will automatically adjust volumetric flow to maintain mass flow constant with variations in temperature and pressure.

The system can also be operated in a constant pressure mode to collect low flow samples. Each of these modes of operation is selectable from the keypad 28.

While the invention has been described in what is presently considered to be a preferred embodiment, many variations and modifications will become apparent to those skilled in the art. Accordingly, it is intended that the invention not be limited to the specific illustrative embodiment but be interpreted within the full spirit and scope of the appended claims.

What is claimed is:

1. A method for controlling an air sampling pump in a system including a central processing unit (CPU) for developing pulse width modulated (PWM) control signals for application to a PWM motor driver connected to an electric motor, the motor being coupled in driving relationship to the air pump, an air filter connected for removing particulate matter from air flowing to the air pump, a revolution per minute (RPM) counter coupled to the motor for providing RPM signals representative of pump speed, a pressure sensor for providing signals representative of differential pressure across the air filter, and a memory operatively associated with the CPU for storing data indicative of relationships between RPM, differential pressure, and air flow rate, the CPU being responsive to a commanded air flow rate for generating a corresponding RPM signal, the method comprising the steps of:

establishing from empirical measurement a family of sets of data relating pump speed to air flow rate as a function of differential pressure across the air filter and storing the data in the CPU memory;

initiating operation of the pump at a selected speed corresponding to a desired air flow rate and selected differential pressure across the air filter;

measuring actual differential pressure across the air filter and identifying a pair of sets of differential pressure values in the stored data which bracket the actual measured differential pressure;

locating the desired air flow rate and corresponding pump RPM value for each of the identified pair of sets of differential pressure values;

extrapolating from the located RPM values a new value of RPM for delivering the desired air flow rate at the actual measured value of differential pressure; and regulating the pump operation at the new RPM value.

2. The method of claim 1 and including the step of measuring the time for each cycle of pump operation and converting the measured time to RPM values for regulating motor operation.

3. The method of claim 1 and including the steps of:

measuring air pressure and temperature at the pump;

computing a volumetric air flow rate corresponding to the desired flow rate at the measured pressure and temperature for constant mass flow; and adjusting pump operation to maintain mass flow at a value corresponding to the desired flow rate.

4. A method for controlling an air sampling pump connected for drawing air through a particulate filter at a selected volumetric flow rate comprising the steps of:

creating a table of data correlating pump speed to volumetric air flow rate as a function of air pressure drop across the filter; and monitoring air pressure drop across the filter during pump operation and adjusting pump speed to a value selected from the table corresponding to the selected volumetric flow rate and monitored air pressure.

5. The method of claim 4 and including the steps of:

measuring air pressure and temperature at the pump;

computing a volumetric air flow rate corresponding to the desired flow rate at the measured pressure and temperature for constant mass flow; and adjusting pump operation to maintain mass flow at a value corresponding to the desired flow rate.

6. The method of claim 4 and including the step of:

computing pump speed by measuring a time duration for one pump cycle and converting the measured time duration to speed.

7. A method for controlling an air sampling pump connected for drawing air through a particulate filter at a selected volumetric flow rate comprising the steps of:

creating a table of data correlating pump speed to volumetric air flow rate as a function of air pressure drop across the filter;

monitoring air pressure drop across the filter during pump operation and adjusting pump speed to a value selected from the table corresponding to the selected volumetric flow rate and monitored air pressure; and wherein the step of creating a table of data includes the steps of:

replacing the particulate filter with a variable orifice control valve;

coupling the pump to a flow meter standard for measuring volumetric air flow rate through the pump;

energizing the pump at each of a plurality of selected operating speeds and measuring the volumetric flow rate at each selected speed using the flow meter;

for each of the selected operating speeds, adjusting the control valve to establish a selected pressure drop across the variable orifice; and correlating the measured flow rate and operating speeds as a function of pressure drop to create the table of data.

\* \* \* \* \*